United States Patent
Shang et al.

(10) Patent No.: US 10,763,645 B2
(45) Date of Patent: Sep. 1, 2020

(54) LASER GENERATION IMPORTING DEVICE APPLIED TO HUMAN BODY

(71) Applicant: Hua Shang, Nanjing, Jiangsu (CN)

(72) Inventors: Hua Shang, Nanjing (CN); Zhiwen Wang, Nanjing (CN); Xinjie Lv, Nanjing (CN)

(73) Assignee: Hua Shang, Nanjing (CN)

( * ) Notice: Subject to any disclaimer, the term of this patent is extended or adjusted under 35 U.S.C. 154(b) by 0 days.

(21) Appl. No.: 16/027,668

(22) Filed: Jul. 5, 2018

(65) Prior Publication Data
US 2018/0342854 A1     Nov. 29, 2018

Related U.S. Application Data

(63) Continuation of application No. PCT/CN2017/101377, filed on Sep. 12, 2017.

(30) Foreign Application Priority Data

Dec. 28, 2016 (CN) .......................... 2016 1 1236994

(51) Int. Cl.
*H01S 5/40* (2006.01)
*H01S 5/042* (2006.01)
(Continued)

(52) U.S. Cl.
CPC ............ *H01S 5/4087* (2013.01); *A61N 5/062* (2013.01); *H01S 5/02284* (2013.01);
(Continued)

(58) Field of Classification Search
CPC ............... H01S 5/4087; H01S 5/02423; H01S 5/02415; H01S 5/0267; H01S 5/4012; H01S 5/4075; H01S 5/4081
See application file for complete search history.

(56) References Cited

U.S. PATENT DOCUMENTS 5,099,487 A * 3/1992 Rickey .................... F25B 21/02
                                                          165/170
5,784,183 A * 7/1998 Aoki ..................... B82Y 20/00
                                                           398/79
(Continued)

FOREIGN PATENT DOCUMENTS

CN     1564404 A     1/2005
CN     103022864 A   4/2013
(Continued)

OTHER PUBLICATIONS

Nov. 1, 2017 International Search Report issued in International Patent Application No. PCT/CN2017/101377.
(Continued)

*Primary Examiner* — Tod T Van Roy
(74) *Attorney, Agent, or Firm* — Hauptman Ham, LLP

(57) ABSTRACT

A laser generation importing device adapted to be applied to the human body includes a tunable laser device. The tunable laser device includes a semiconductor chilling plate which is capable of adjusting temperature, the semiconductor chilling plate is provided with a laser emission array, and the laser emission array includes multiple independent laser units which are capable of emitting different wavelengths.

15 Claims, 6 Drawing Sheets

(51) Int. Cl.
*H01S 5/024* (2006.01)
*H01S 5/022* (2006.01)
*H01S 5/068* (2006.01)
*A61N 5/06* (2006.01)
*A61N 5/067* (2006.01)
*H01S 5/06* (2006.01)

(52) U.S. Cl.
CPC ...... *H01S 5/02288* (2013.01); *H01S 5/02415* (2013.01); *H01S 5/02476* (2013.01); *H01S 5/042* (2013.01); *H01S 5/068* (2013.01); *H01S 5/4012* (2013.01); *A61N 2005/063* (2013.01); *A61N 2005/067* (2013.01); *A61N 2005/0652* (2013.01); *H01S 5/02423* (2013.01); *H01S 5/0612* (2013.01)

(56) References Cited

U.S. PATENT DOCUMENTS

| | | | | |
|---|---|---|---|---|
| 2002/0070359 A1* | 6/2002 | Kai | ............... | H01S 5/4031 250/504 R |
| 2004/0184753 A1* | 9/2004 | Teramura | ............. | G02B 6/4248 385/128 |
| 2005/0168819 A1* | 8/2005 | Vail | ............... | H01S 5/40 359/557 |
| 2005/0226284 A1 | 10/2005 | Tanaka et al. | | |
| 2015/0258348 A1* | 9/2015 | Schenker | ............. | A61N 5/0622 607/89 |
| 2016/0204569 A1* | 7/2016 | Kuzukami | ............ | H01S 3/0014 372/20 |
| 2017/0279246 A1* | 9/2017 | Muendel | ............... | B23K 26/703 |
| 2017/0302055 A1* | 10/2017 | Pescod | ................ | H01S 5/02415 |
| 2018/0013264 A1* | 1/2018 | Tanaka | ............... | H01S 5/02415 |
| 2018/0054067 A1* | 2/2018 | Peng | ....................... | H02J 7/007 |
| 2018/0069558 A1* | 3/2018 | Maki | ...................... | G04F 5/145 |

FOREIGN PATENT DOCUMENTS

| | | |
|---|---|---|
| CN | 105449506 A | 3/2016 |
| CN | 205144725 U | 4/2016 |
| CN | 106532431 A | 3/2017 |

OTHER PUBLICATIONS

Nov. 1, 2017 Written Opinion issued in International Patent Application No. PCT/CN2017/101377.

* cited by examiner

LASER GENERATION IMPORTING DEVICE APPLIED TO HUMAN BODY

TECHNICAL FIELD

The present invention relates to the field of laser technology, and in particular to a laser generation importing device applied to the human body.

BACKGROUND ART

At present, multi-wavelength laser units, especially the multi-wavelength laser units with continuously tunable wavelengths, are extensively required in such scientific research fields as biology and materials and in such industrial fields as medical treatment and detection. The commonly seen laser units now are mostly semiconductor laser units and solid-state laser units. Due to the limitations of laser emission mechanisms and laser material performances, only a limited number of output wavelengths are available, with a narrow tunable range of usually only several nanometers, which greatly limits the application in the above fields. For example, in the process of treating tumors by using a photodynamic therapy, a photosensitizer is additionally needed to generate singlet oxygen to kill cancer cells. Since the difference between absorption peaks of laser by different photosensitizers is great, a better curative effect can only be achieved via a laser therapeutic instrument with different wavelengths or even with arbitrarily tunable wavelengths.

One of the approaches to generate laser with tunable wavelengths is to use a frequency conversion technology, for example, frequency multiplication, beat frequency, optical parametric oscillation, etc. At present, an optical parametric oscillator pumped by an all-solid-state laser unit adopts such crystals as BBO (barium boron oxide crystal), LBO (lithium baron), KTP or PPLN (periodic polarized lithium niobate) as a nonlinear frequency conversion device, such conditions as angle and position of crystals are adjusted in a mechanical manner, then laser with tunable wavelength can be generated, arbitrary wavelengths can be output based on requirements, thereby satisfying the requirements on wavelength and power in the above applications. However, since nonlinear crystals must adjust the wavelengths in a mechanically adjusted manner, leading to the fact that the device is internally provided with such parts as a stepping motor, a rotating or displacing platform, therefore, the structure is complex, the size is large, the tuning speed is low, and the stability and reliability are inferior. Another approach to generate laser with tunable wavelengths is to adopt a dye laser unit, tunable laser can be generated by utilizing the advantage that the spectral range emitted by liquid fuel is wide, the tunable range can reach up to hundreds of nanometers, the power can reach up to thousands of watts, however, the size is large and dye is harmful to human bodies and needs to be replaced periodically, therefore, such approach is rarely adopted now.

SUMMARY OF THE INVENTION

In view of this, one object of the present invention is to provide a laser generation importing device applied to the human body. The present invention provides a tunable laser device with a wide wavelength range, continuously tunable wavelengths and a compact and reliable structure, so as to overcome the problems of complex structure, narrow tunable range of wavelengths and low reliability of the tunable laser unit in the prior art.

The object of the present invention is realized through the following technical solution:

A laser generation importing device applied to the human body includes a tunable laser device, wherein the tunable laser device includes a semiconductor chilling plate which is capable of adjusting temperature, the semiconductor chilling plate is provided with a laser emission array, and the laser emission array includes multiple independent laser units which are capable of emitting different wavelengths.

Further, the wavelength difference of the wavelengths emitted by two laser units which emit adjacent wave bands is less than or equal to the greatest adjustment wavelength of the semiconductor chilling plate.

Further, multiple laser units are connected to a same power source in parallel via wires, and each laser unit is provided with a switch which can independently control the opening and closing of the laser unit.

Further, the semiconductor chilling plate is arranged on an upper end face of a liquid cooling metal sheet, the upper end face of the liquid cooling metal sheet is provided with a cooling liquid channel, and the cooling liquid channel is internally provided with a liquid coolant which is capable of exporting heat from the semiconductor chilling plate.

Further, the liquid cooling metal sheet is provided with a cooling liquid injection opening connected with one end of the cooling liquid channel and a cooling liquid recovering opening connected with the other end of the cooling liquid channel.

Further, the semiconductor chilling plate, multiple laser units and the liquid cooling metal sheet are all encapsulated in a sealed box, and the sealed box is provided with multiple light emitting holes which are used for outputting the light emitted by the laser unit.

Further, the wavelength values of the lights emitted by multiple semiconductor laser units are of an arithmetic progression, and the value of the wavelength difference of adjacent wavelengths is smaller than the value of the greatest adjustment wavelength of the semiconductor chilling plate.

Further, the light emitting direction of each laser unit in the sealed box is provided with a lens used for converging the light emitted by the laser unit, and multiple lenses corresponding to multiple laser units constitute a lens array.

Further, each light emitting hole is connected with an extracted optical fiber which extends outside the sealed box 1, a coupler is arranged between the extracted optical fiber and the lens, the lights emitted by multiple semiconductor laser units in the laser emission array are converged to the miniature or small-sized coupler via the lens array, and the coupler then couples the lights to the extracted optical fiber.

Further, the coupler is in butt joint with the extracted optical fiber.

Further, the tunable laser device is connected with a beam combiner which can couple multiple beams of light into one beam of light and then output, and multiple beams of extracted optical fibers led out via multiple light emitting holes are coupled and converged into a beam of optical fiber in the beam combiner.

Further, the laser unit is a semiconductor laser unit.

Further, the wavelengths of the lights emitted by multiple semiconductor laser units are all in a range of 400 nm to 2000 nm.

Further, the value of wavelength difference of adjacent wavelengths is 14.

Further, the laser generation importing device applied to the human body further includes a light conducting device which is capable of importing light into the human body, wherein the light conducting device is connected with the tunable laser device, such that the laser emitted by the tunable laser device is guided into the human body via the light conducting device.

The Present Invention at Least has the Following Beneficial Effects:

(1) In the present invention, multiple laser units which emit different wavelengths or discrete wavelengths form an array to serve as a laser light source for generating multiple wavelengths, thereby realizing large-scale wavelength adjustment through switching the operating laser units. Then precision adjustment of wavelengths is realized through precision temperature control of the semiconductor chilling plate, the tunable laser device in the present invention can be tuned in any wavelength range, that is, the tunable laser device can output laser with continuously tunable wavelengths, then the lasers are converged into one optical fiber to output via multiple paths of optical fiber beam combiner (or in other modes, such as a space coupling method).

(2) The wavelength difference between laser units is less than or equal to the greatest adjustment wavelength of the semiconductor chilling plate, such that the tunable laser device in the present invention can be adjusted to have any wavelength, and the application is not limited at all.

(3) With all the laser units being connected in parallel to the same utility power, time division multiplexing or time-sharing power supply is realized, thereby lowering the total energy consumption and the strict requirement on heat dissipation.

(4) Through the connection between the semiconductor chilling plate and liquid coolant, heat can be exported timely, two stages of cooling including semiconductor cooling and liquid cooling enable the tunable laser device to be subjected to large-scale precision temperature control and further to wavelength tuning, and liquid cooling is beneficial for flexible temperature adjustment of the semiconductor chilling plate.

(5) The semiconductor chilling plate and the laser unit are encapsulated by a sealed box, thereby greatly reducing the influence on the environment, leading to more precise adjustment, and lowering the total energy consumption.

(6) The laser emitted by multiple laser units in the laser emission array is output in a beam-combining and coupling manner through multiple optical fibers. The laser device is compact in structure, high in reliability, convenient in use and capable of satisfying the demands on tunable laser units in such fields as biology and medical treatment. In the tunable laser device, the laser emission array is encapsulated and then the lasers are coupled via an optical fiber and output, such that the size of the tunable laser unit is decreased, and the reliability is greatly enhanced.

In short, for the tunable laser device in the present invention, a broad-spectrum continuous tunable characteristic of wavelengths is realized through time division multiplexing and large-scale precision temperature control, and the shortcoming of a narrow tunable range of the wavelengths output by a single semiconductor laser unit is overcome.

1. sealed box, 2. light emitting hole, 3. wire, 4. semiconductor laser unit, 5. semiconductor chilling plate, 6. liquid cooling metal sheet, 7. lens array, 8. lens, 9. coupler, 10. optical fiber guide wire, 21. extracted optical fiber, 30. light coupler, 40. tunable laser device, 50. beam combiner, 61. cooling liquid channel, 62. injection opening, 63. recovery opening.

DETAILED DESCRIPTION OF THE EMBODIMENTS

A clear and complete description will be given below on the technical solutions of the embodiments in the present invention, and apparently the embodiments described below are only a part but not all of the embodiments of the present invention. A detailed description of the embodiments of the present invention below is not deemed as a limitation on the scope of protection of the present invention, and only represents the selected embodiments of the present invention. Based upon the embodiments of the present invention, all the other embodiments which can occur to those skilled in the art without any inventive efforts shall all fall into the scope of protection of the present invention.

Embodiment 1

As shown in FIG. 1 to FIG. 5, a laser generation importing device applied to the human body includes a tunable laser device. The tunable laser device 40 includes a semiconductor chilling plate 5 (TEC) which is capable of adjusting temperature and a laser emitting array, the laser emission array includes multiple independent semiconductor laser units 4 which are capable of emitting different wavelengths. All the semiconductor laser units 4 are welded on the upper surface of the semiconductor chilling plate 5 via a metal welding manner. The semiconductor chilling plate 5 can form two working modes including cooling and heating through adjusting the voltage or adjusting the positive and negative control of voltage, thereby realizing temperature adjustment within a range of −20° to +40°. While along with the change of temperature, the wavelength of the semiconductor laser unit 4 also changes. Namely, the wavelength correspondingly increases along with the rise of temperature. The temperature coefficient is generally from 0.2 nm/K to 0.3 nm/K. Therefore, in a range of −20° to +40°, the semiconductor laser unit 4 has a temperature tunable range of about 15 nm.

Figure 3:
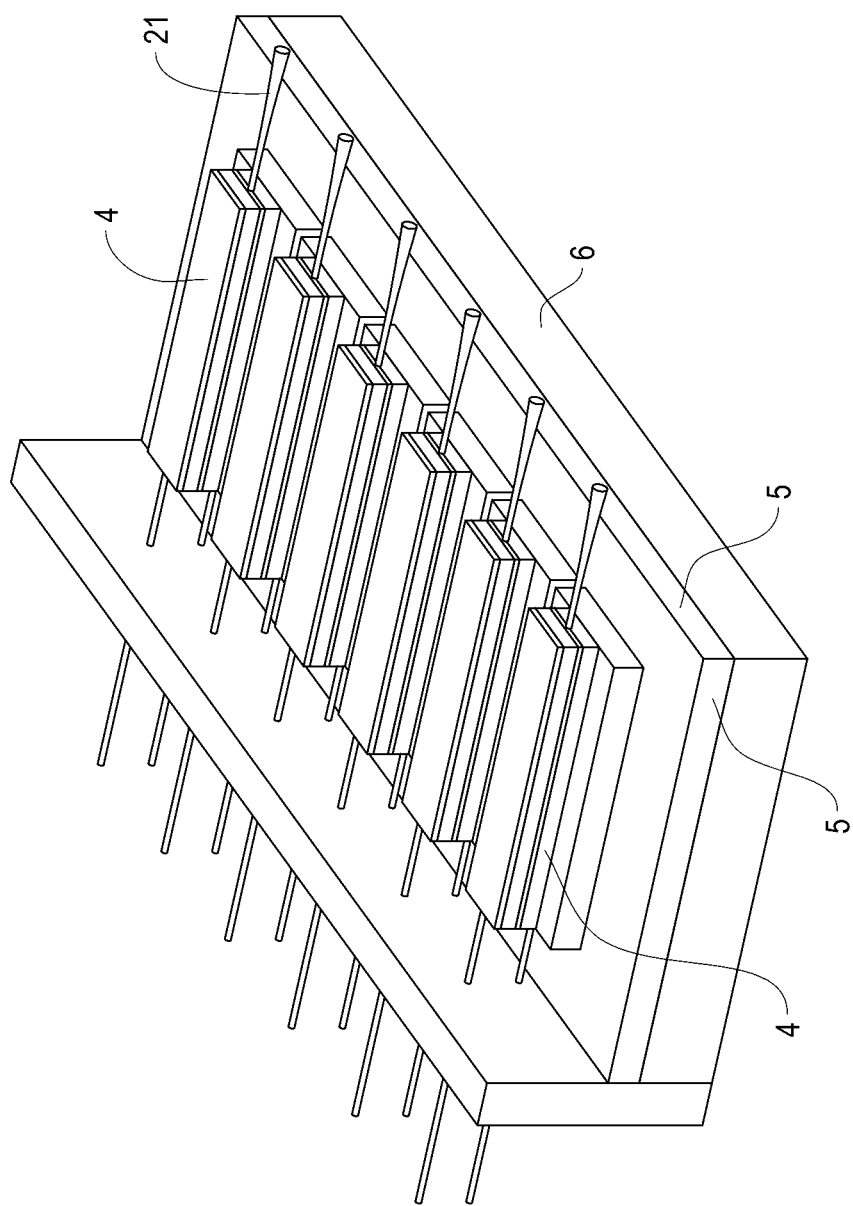
FIG. 3 is a schematic diagram of an internal encapsulating structure of the tunable laser device in the embodiments of the present invention.

The wavelengths emitted by multiple semiconductor laser units 4 are different, then the wavelength difference of the wavelengths emitted by two laser units which emit adjacent wavelengths/wave bands is less than or equal to the greatest adjustment wavelength of the semiconductor chilling plate 5. That is, the central wavelength of the semiconductor laser unit of different wavelengths is selected based on the temperature control range, the requirement that semiconductor laser units with adjacent wavelengths can be continuously tunable is satisfied when the temperature is adjusted in a large scale, as shown in FIG. 3, such that the tunable laser device can emit lights of any arbitrary wavelength. Namely, a large-scale adjustment of the wavelengths can be realized by switching to select different semiconductor laser units 4, and a small-scale or precision-scale adjustment of the wavelengths can be realized through the semiconductor chilling plate 5.

Figure 4:
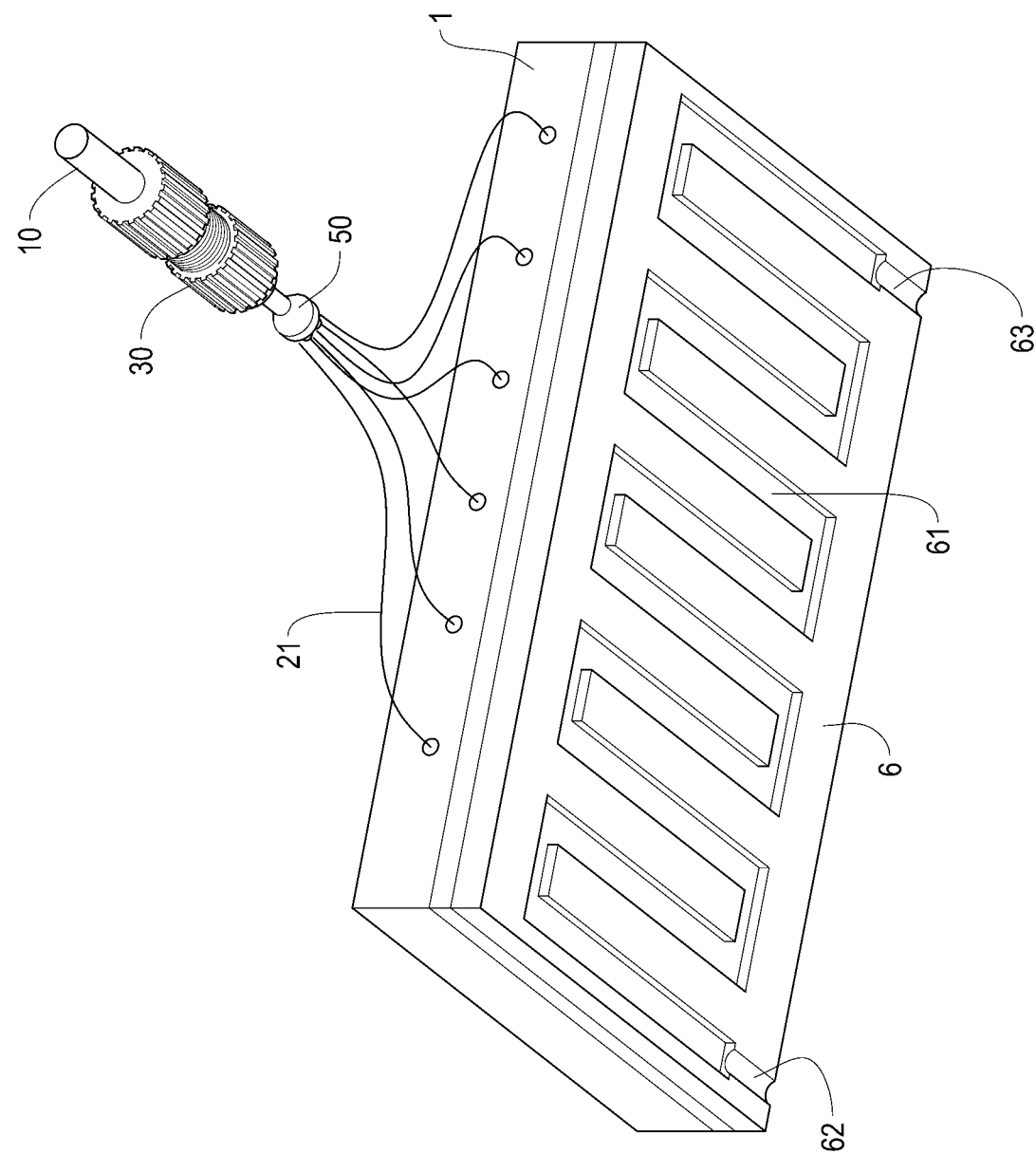
FIG. 4 is a structural schematic diagram of the tunable laser device in the embodiments of the present invention with part of the parts being removed.

The lower surface of the semiconductor chilling plate 5 is connected with a liquid cooling metal sheet 6 (namely, the metal sheet capable of placing a liquid coolant). The upper end face of the liquid cooling metal sheet is provided with a cooling liquid channel 61 which is in a broken line shape or an S shape. The cooling liquid channel 61 is internally provided with liquid coolant (namely, cooling liquid) which is capable of exporting heat in the semiconductor chilling plate, as shown in FIG. 4. That is, the liquid coolant or cooling liquid is placed between the semiconductor chilling plate 5 and the liquid cooling metal sheet 6, such that the liquid coolant or cooling liquid can export the heat generated in the semiconductor chilling plate 5 to form a secondary cooling mode. Then a large-scale precision temperature control can be performed through two stages of cooling including semiconductor cooling and liquid cooling to realize precision tuning. The cooling liquid can be liquid nitrogen and the like. Other types of cooling liquid can also be selected based on actual requirements.

The liquid cooling metal sheet 6 is provided with a cooling liquid injection opening 62 connected with one end of the cooling liquid channel 61 and a cooling liquid recovering opening 63 connected with the other end of the cooling liquid channel 61. During use, the cooling liquid injection opening can be connected with a cooling liquid storage tank, and the cooling liquid recovering opening can be connected with a cooling liquid recovery tank, such that the liquid coolant inside the tunable laser device can be recycled, and the cooling effect is better. The injection opening 62 and the recovery opening 63 are also correspondingly provided with an inlet and an outlet on the sealed box 1.

Multiple semiconductor laser units 4 are connected to a same power source in parallel via wires. Each semiconductor laser unit 4 is provided with a switch which can independently control the opening and closing of the laser unit, and the laser unit needing to operate can be selected through a multiway switch. Then time division multiplexing or time-sharing power supply can be realized. Namely, when the light of a certain wave band is needed, the corresponding semiconductor laser unit 4 which is capable of emitting light of such a wave band is selected to start, while the other semiconductor laser units 4 are not started, thereby lowering the total energy consumption and the strict requirement on heat dissipation.

The liquid cooling metal sheet 6, the semiconductor chilling plate 5 and multiple semiconductor laser units 4 arranged on the semiconductor chilling plate 5 are all encapsulated in a sealed box 1. Namely, environmental heat exchange can be isolated through the sealed box 1 made of thermal insulation materials, thereby further reducing the cooling and heating amount, and realizing more precise control and energy conservation.

Figure 1:
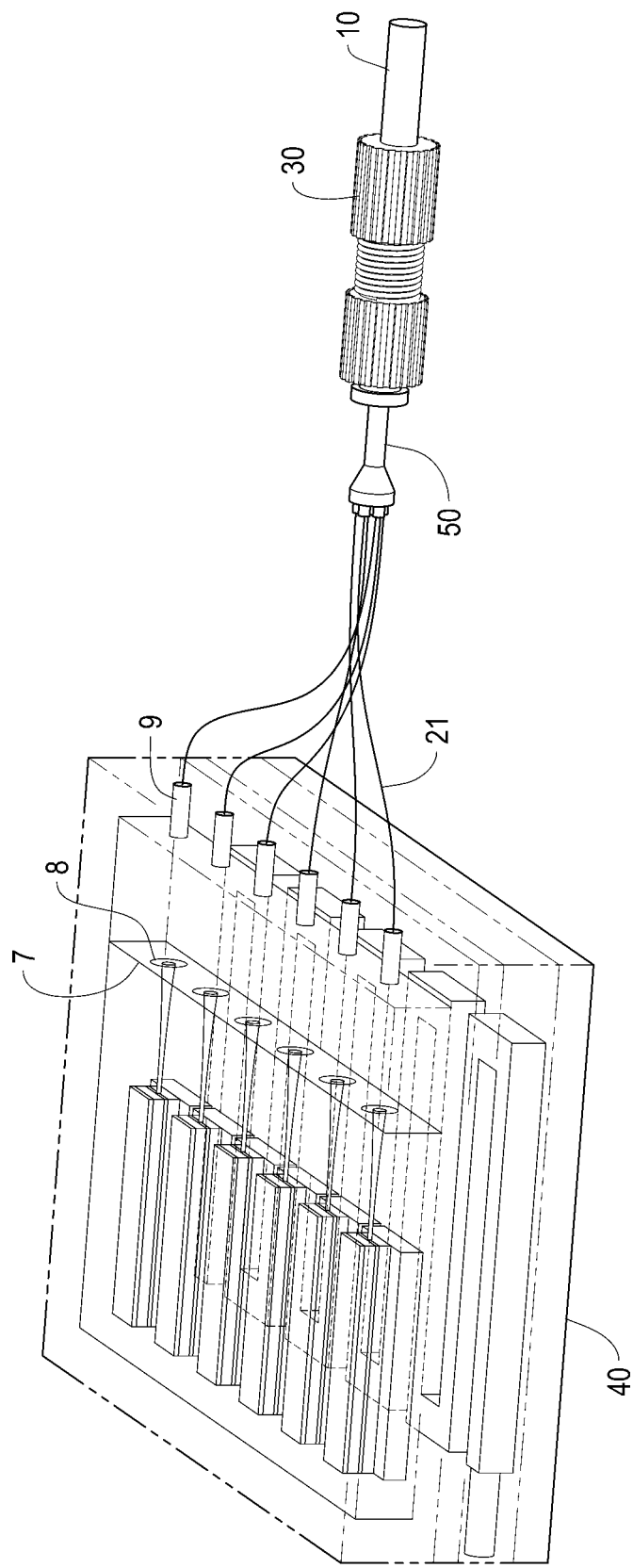
FIG. 1 is a schematic diagram (perspective drawing) of the overall structure of the laser generation conducting device in the embodiments of the present invention.
Figure 2:
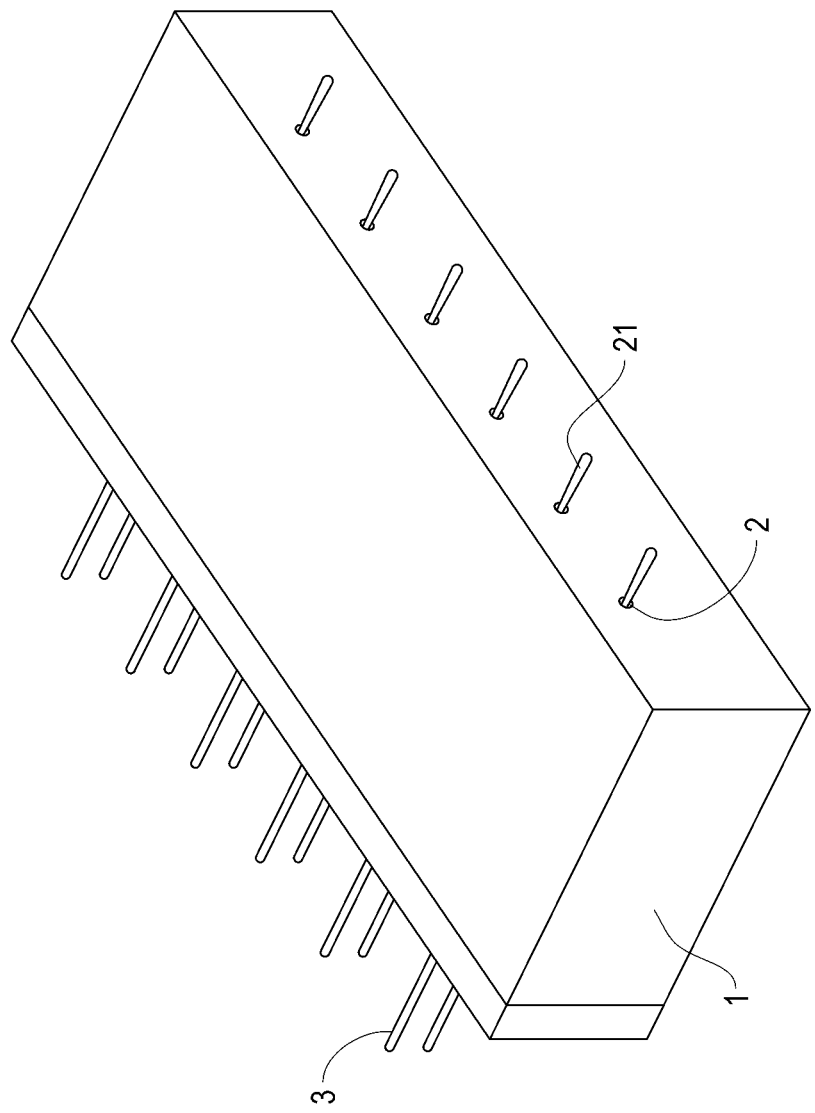
FIG. 2 is a schematic diagram of an external encapsulating structure of the tunable laser device in the embodiments of the present invention.

All the semiconductor laser units 4 are output from the sealed box 1 via wires and are connected to the same utility power. Meanwhile, the sealed box 1 is further provided with multiple light emitting holes 2 which are used for outputting the light emitted by the semiconductor laser unit 4, and each light emitting hole 2 corresponds to a laser transmitting hole (namely, the hole for emitting light) of a semiconductor laser unit 4. As shown in FIG. 1 to FIG. 2, one side of the sealed box 1 can output a wire 3, while the other side can output laser.

Figure 5:
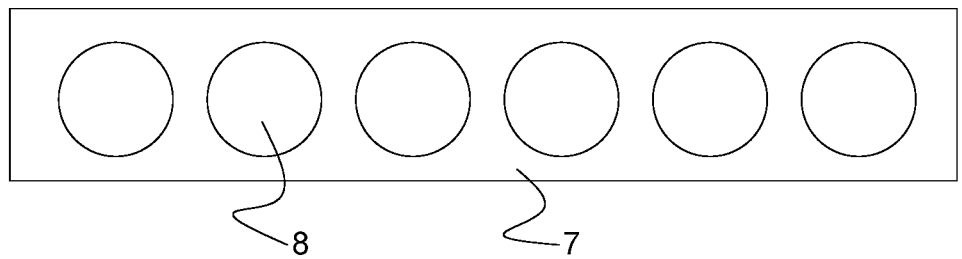
FIG. 5 is a structural schematic diagram of the lens array in the embodiments of the present invention.

As shown in FIG. 1 and FIG. 5, inside the sealed box 1, lenses 8 which can converge light are arranged on the light emitting direction of each semiconductor laser unit 4. Namely, on the same axis with light, multiple lenses 8 corresponding to multiple semiconductor laser units 4 constitute a lens array 7, the lens array 7 can be directly connected to the laser transmitting hole of the semiconductor laser unit 4, and can also be arranged on the light emitting direction of the semiconductor laser unit 4 but is not directly connected with the semiconductor laser unit 4. However, the laser transmitting hole of the semiconductor laser unit 4, the lenses 8 and the light emitting hole 2 on the sealed box 1 are all on the same straight line.

Each light emitting hole 2 is connected with an extracted optical fiber 21 which extends outside the sealed box 1. A coupler 9 is arranged between the extracted optical fiber 21 and the lens 8, as shown in FIG. 1, the lights emitted by multiple semiconductor laser units 4 in the laser emission array are converged to multiple or each (miniature or small-sized) coupler 9 via the lens array 7, and then the coupler 9 couples the lights to the corresponding extracted optical fiber 21.

The tunable laser device 40 is fixedly connected with a beam combiner 50 which can couple multiple beams of light into one beam of light and then output, and multiple beams of extracted optical fibers 21 led out via multiple light emitting holes 2 are coupled and converged into one beam of optical fiber in the beam combiner 50. Namely, the lights emitted by the semiconductor laser unit 4 are transmitted to the coupler 9 via a lens 8, the coupler 9 then transmits the lights to the extracted optical fiber 21, and the extracted optical fiber 21 introduces lights into the beam combiner 50. That is, the lights are coupled into one beam of light in the beam combiner 50 and then output. Preferably, the coupler 9 is arranged on the light emitting hole 2, and then the coupler 9 is in direct butt joint with the extracted optical fiber 21. Namely, one end of the extracted optical fiber 21 is converged into the beam combiner 50, while the other end is in butt joint with the coupler 9.

During specific implementation, based on actual conditions, the current operating requirements can be satisfied if the wavelengths of the light emitted by the semiconductor laser unit 4 are in a range of 400 nm~2000 nm. Preferably, multiple semiconductor laser units 4 are uniformly welded on the semiconductor chilling plate 5 in parallel to form a laser emission array. The wavelengths of the lights emitted by multiple semiconductor laser units 4 are of an arithmetic progression. The value of the wavelength difference of adjacent wavelengths is smaller than the value of the greatest adjustment wavelength of the semiconductor chilling plate 5. For example, the wavelength difference of adjacent wavelengths is 14.

The semiconductor laser unit 4 in the present embodiment can be a single-tube semiconductor laser unit or a multi-tube semiconductor laser unit. The size can be of several hundreds of microns, and a required size can be made based on actual demands.

For the tunable laser device in the present invention, since the output power of the semiconductor laser unit 4 is high, the calorific value is great, thus a cooling mode is mainly adopted for temperature control. When temperature rise is needed, the liquid cooling mode can be stopped, and TEC voltage is reversed to generate heat. In short, precise temperature control can be realized through liquid coolant and semiconductor chilling plate.

In specific use, the required laser wavelength is set to λ. The light source of a tunable laser device is opened. The semiconductor laser unit closest to the set wavelength λ is selected to operate after being energized. Then the wavelength is adjusted to the set wavelengthλ through precise temperature control. Finally, the laser at a given wavelength is exported via the extracted optical fiber.

Embodiment 2

Figure 6:
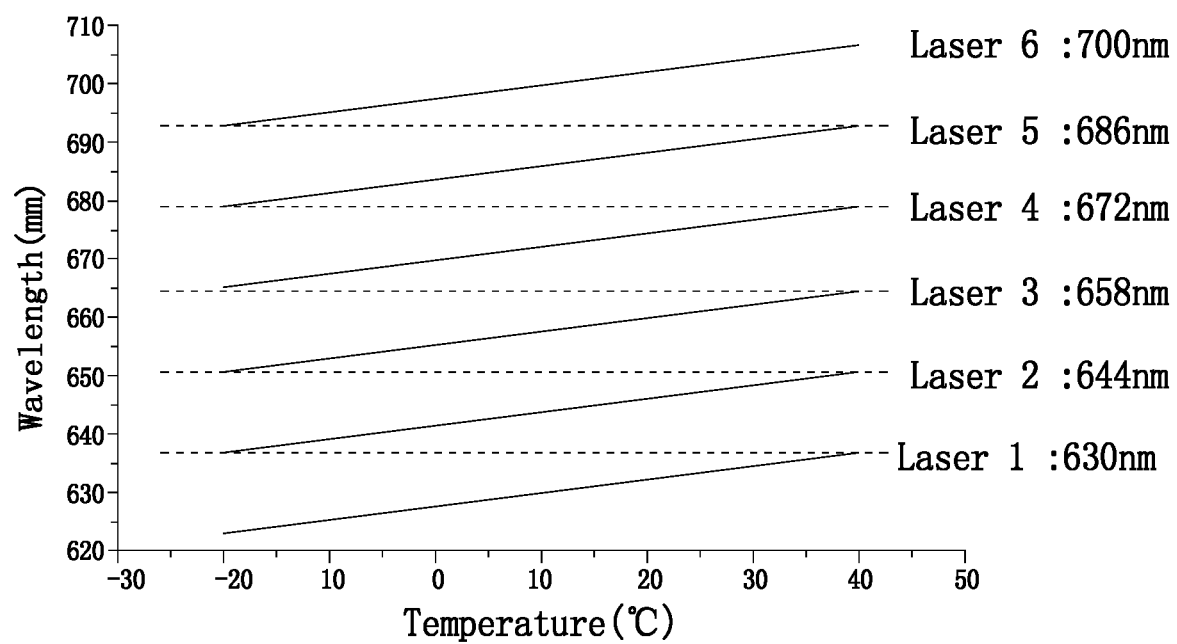
FIG. 6 is a curve diagram of wavelength tuning of multiple semiconductor laser units in the embodiments of the present invention.

As shown in FIG. 6, based on the tunable laser device in Embodiment 1, for example, for realizing the output of continuous tunable laser in a wave band with the wavelengths being in a range of 623 nm-707 nm, firstly the semiconductor laser unit 4 which outputs six discrete wavelengths including 630 nm, 644 nm, 658 nm, 672 nm, 686 nm, 700 nm at a temperature of 10° is selected. Namely, six semiconductor laser units 4 with the wavelength difference of 14 nm are selected, and then in a sequence from small wavelength to big wavelength, the six semiconductor laser units 4 are named as follows: Laser 1, Laser 2, Laser 3, Laser 4, Laser 5 and Laser 6. Along with the temperature change, the wavelength of the semiconductor laser unit 4 also changes, the relationship between the temperature and the wavelength is 0.2 nm/K~0.3 nm/K. Therefore, when the semiconductor chilling plate 5 can adjust the temperature in a range of −20° to +40°, the semiconductor laser unit 4 then has a temperature tunable range of about 15 nm.

Through large-scale wavelength selection and time division multiplexing of six semiconductor laser units 4, and through precision temperature control of the semiconductor chilling plate 5, at a temperature range of −20° to +40°, the wavelengths of the tunable laser device can be continuously tuned in a range of 623 nm-707 nm. That is, the tunable range of each semiconductor laser unit 4 is basically as follows: Laser 1: 623 nm~637 nm, Laser 2: 637 nm~651 nm, Laser 3: 651 nm~665 nm, Laser 4: 665 nm~679 nm, Laser 5: 679 nm~693 nm, Laser 6: 693 nm~707 nm.

For example, if the laser with a wavelength of 670 nm is required to be output, as shown in FIG. 1, a semiconductor laser unit 4 (laser 4) is selected to start to serve as an operating laser unit through a power supply opening, the output wavelength of laser 4 at a temperature of 10° is 672 nm, the temperature of the semiconductor chilling plate 5 is adjusted to a temperature of +3°, the output wavelength of laser 4 is 670 nm. If the wavelength is required to be adjusted to 660 nm, an independent switch on each semiconductor laser unit 4 is controlled to select laser 3 as an operating laser unit, the output wavelength of laser 3 at a temperature of 10° is 658 nm, then the temperature is controlled to a temperature of +20°, and the output wavelength is 660 nm.

During specific use, the quantity of the semiconductor laser unit 4 is selected based on actual requirements, the adjustment of large-scale wavelengths is realized through selecting the semiconductor laser unit 4. And then based on the corresponding relationship between the wavelengths and temperature, for the adjustment of wavelengths in a precise range, the final output wavelength can be realized through adjusting the temperature. During specific implementation, the temperature change of the semiconductor chilling plate 5 can be converted into wavelengths and then marked, thereby facilitating the adjustment by users.

Figure 7:
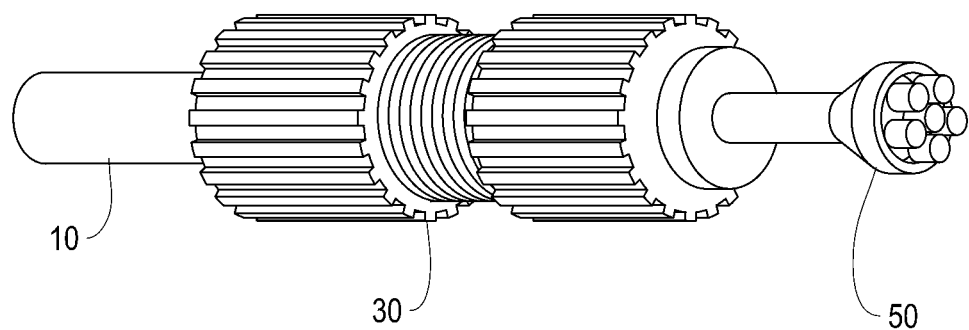
FIG. 7 is a schematic diagram of an external structure at the connecting point between the tunable laser device and the optical fiber guide wire in the embodiments of the present invention.
Figure 8:
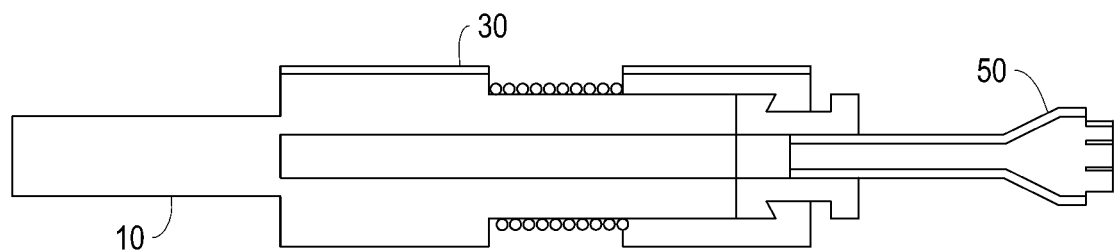
FIG. 8 is a structural schematic diagram of a cross section at the connecting point between the tunable laser device and the optical fiber guide wire in the embodiments of the present invention.

In the photodynamic tumor therapy, as shown in FIG. 1, FIG. 7 to FIG. 8, a light conducting device 10 can enter a lesion of the human body as long as the tunable laser device 40 is connected with the light conducting device 10 which conducts light. And then the light emitted by the tunable laser device 40 is conducted to the lesion. During specific use, multiple beams of light emitted by the tunable laser device 40 are coupled into one beam of light via a beam combiner 50 and then output. And then the beam combiner 50 is connected with the light conducting device 10 via a light coupler 30, such that the coupled one beam of light is transmitted to the light conducting device 10 via a light coupler 30. The light conducting device 10 enters into or is inserted into the lesion under the guidance of clinical imaging. Through adjusting a broad-spectrum array, a time division multiplexing tunable laser device 40 outputs the laser with a wavelength which is required by a certain photosensitizer, such that the light conducting device 10 irradiates the laser with corresponding wavelength onto the tumor which has been injected with a photosensitive medicine, the photosensitive medicine inside the tumor is subjected to photochemical reaction to generate singlet oxygen and further lead to necrosis and apoptosis of the tumor, thereby achieving the aim of treating tumors.

The embodiments described above are merely preferred embodiments of the present invention, rather than limiting the present invention. For those skilled in the art, various modifications and transformations can be made to the present invention. Any modification, equivalent substitution and improvement made within the spirit and principle of the present invention shall all fall within the protection scope of the present invention.

The invention claimed is:

1. A laser generation importing device adapted to a human body, comprising
    tunable laser device capable of emitting laser, wherein the tunable laser device comprises
        a semiconductor chilling plate capable of adjusting temperature, and a laser emission array on the semiconductor chilling plate, wherein the laser emission array comprises multiple independent laser units capable of emitting different wavelengths;
        wherein the wavelength difference of the wavelengths emitted by two laser units which emit adjacent wave bands is less than or equal to the greatest adjustment wavelength of the semiconductor chilling plate; and
        multiple laser units are connected to a same power source in parallel via wires, and each laser unit is provided with a switch which can independently control the opening and closing of the laser unit,
    wherein the semiconductor chilling plate, the multiple laser units and a liquid cooling metal sheet are all encapsulated in a sealed box, and the sealed box is provided with multiple light emitting holes configured to output light emitted by the laser units,
    the sealed box is made of thermal insulation materials, thereby further reducing a coding and heating amount, and realizing a precise control and energy conservation, the tunable laser device is connected with a beam combiner, and multiple extracted optical fibers led out via the multiple light emitting holes are coupled and converged into one output in the beam combiner, the light emitted by one of the laser units is transmitted to a coupler via a lens, the coupler then transmits the light to one of the extracted optical fibers, and the extracted optical fiber introduces the light into the beam combiner, the coupler is arranged on one of the light emitting holes, and then the coupler is in direct butt joint with the extracted optical fiber.

2. The laser generation importing device of claim 1 wherein the semiconductor chilling plate is on an upper end face of the liquid cooling metal sheet, the upper end face of the liquid cooling metal sheet is constructed to comprise a cooling liquid channel, wherein the cooling liquid channel is internally provided with a liquid coolant capable of exporting heat from the semiconductor chilling plate.

3. The laser generation importing device of claim 2, wherein the cooling liquid channel is constructed in the liquid cooling metal sheet in a broken line shape or an S shape, and the liquid coding metal sheet is further constructed to comprise a cooling liquid injection opening and a cooling liquid recovering opening which are respectively connected to two ends of the cooling liquid channel.

4. The laser generation importing device of claim 3, wherein the laser units are semiconductor laser units;

the wavelength values of the light emitted by the multiple semiconductor laser units are of an arithmetic progression, and the value of the wavelength difference of adjacent wavelengths is smaller than the value of the greatest adjustment wavelength of the semiconductor chilling plate.

5. The laser generation importing device of claim 2, wherein the laser units are a semiconductor laser units;

the wavelength values the light emitted by the multiple semiconductor laser units are of an arithmetic progression, and the value of the wavelength difference of adjacent wavelengths is smaller than the value of the greatest adjustment wavelength of the semiconductor chilling plate.

6. The laser generation importing device of claim 1, wherein the light emitting direction of each of the other laser units in the sealed box is provided with a lens used for converging the light emitted by the laser units, and each lens is a part of a lens array comprising multiple lenses corresponding to the multiple laser units.

7. The laser generation importing device of claim 6, wherein each of the other light emitting holes is connected with one of the other extracted optical fibers which extends outside the sealed box, couplers are arranged between each of the other extracted optical fibers and each one of the lenses, the light emitted by the multiple laser units in the laser emission array are converged to the couplers, and the couplers then couples the light to the extracted optical fibers.

8. The laser generation importing device of claim 7, wherein the couplers are in butt joint with the extracted optical fibers.

9. The laser generation importing device of claim 8, wherein the laser units are a semiconductor laser units:

the wavelength values of the light emitted by the, multiple semiconductor laser units are of an arithmetic progression, and the value of the wavelength difference of adjacent wavelengths is smaller than the value of the greatest adjustment wavelength of the semiconductor chilling plate.

10. The laser generation importing device of claim 7, wherein the laser units are a semiconductor laser units;

the wavelength values of the light emitted by the multiple semiconductor laser units are of an arithmetic progression, and the value of the wavelength difference of adjacent wavelengths is smaller than the value of the greatest adjustment wavelength of the semiconductor chilling plate.

11. The laser generation importing device of claim 6, wherein the laser units are a semiconductor laser units;

the wavelength values of the light emitted by the multiple semiconductor laser units are of an arithmetic progression, and the value of the wavelength difference of adjacent wavelengths is smaller than the value of the greatest adjustment wavelength of the semiconductor chilling plate.

12. The laser generation importing device of claim 1, wherein the laser units are semiconductor laser units;

the wavelength values of the light emitted by the multiple semiconductor laser units are of an arithmetic progression, and the value of the wavelength difference of adjacent wavelengths is smaller than the value of the greatest adjustment wavelength of the semiconductor chilling plate.

13. The laser generation importing device of claim 1, further comprising a light conducting device adapted to import light into the human body, wherein the light conducting device is connected with the tunable device, such that the laser emitted by the tunable device is guided into the human body via the light conducting device.

14. The laser generation importing device claim 1, wherein the laser units are a semiconductor laser units;

the wavelength values of the light emitted by the multiple semiconductor laser units are of an arithmetic progression, and the value of the wavelength difference of adjacent wavelengths is smaller than the value of the greatest adjustment wavelength of the semiconductor chilling plate.

15. The laser generation importing device of claim 1, wherein the semiconductor chilling plate is on an upper end face of the liquid cooling metal sheet.

* * * * *